United States Patent [19]
Sunderland

[11] Patent Number: 5,955,153
[45] Date of Patent: *Sep. 21, 1999

[54] PRODUCTION OF CARRIERS FOR SURFACE PLASMON RESONANCE

[75] Inventor: Robert Frank Sunderland, Berkhamsted, United Kingdom

[73] Assignee: Johnson & Johnson Clinical Diagnostics, Inc., Rochester, N.Y.

[*] Notice: This patent is subject to a terminal disclaimer.

[21] Appl. No.: 08/723,714

[22] Filed: Sep. 30, 1996

Related U.S. Application Data

[63] Continuation of application No. 08/567,821, Dec. 6, 1995, abandoned, which is a continuation of application No. 08/306,083, Sep. 14, 1994, abandoned.

[30] Foreign Application Priority Data

Oct. 1, 1993 [GB] United Kingdom .................. 9320207

[51] Int. Cl.⁶ ..................................................... H05H 1/00
[52] U.S. Cl. ...................... 427/535; 427/539; 427/126.5; 427/376.7; 427/419.1
[58] Field of Search ..................................... 427/535, 539, 427/126.5, 376.7, 419.1

[56] References Cited

U.S. PATENT DOCUMENTS

| | | | |
|---|---|---|---|
| 4,948,225 | 8/1990 | Rider et al. | 350/96.34 |
| 4,992,385 | 2/1991 | Godfrey | 436/525 |
| 4,997,278 | 3/1991 | Finlan et al. | 356/128 |
| 5,023,053 | 6/1991 | Finlan | 422/82.05 |
| 5,035,863 | 7/1991 | Finlan | 422/82.05 |
| 5,047,213 | 9/1991 | Finlan et al. | 422/82.11 |
| 5,055,265 | 10/1991 | Finlan | 422/82.05 |
| 5,064,619 | 11/1991 | Finlan | 422/82.05 |
| 5,151,956 | 9/1992 | Bloemer | 385/11 |
| 5,273,788 | 12/1993 | Yu | 427/554 |
| 5,449,918 | 9/1995 | Krull et al. | 250/458.1 |
| 5,474,815 | 12/1995 | Sunderland | 427/576 |

FOREIGN PATENT DOCUMENTS

257955  3/1988  European Pat. Off. ....... G01N 81/84

*Primary Examiner*—Benjamin Utech

[57] ABSTRACT

A carrier for surface plasmon resonance is prepared by coating a silver layer on the carrier surface, followed by heating the material for a time sufficient to anneal it.

9 Claims, 1 Drawing Sheet

PRODUCTION OF CARRIERS FOR SURFACE PLASMON RESONANCE

This application is a continuation of U.S. patent application Ser. No. 08/567,821, filed Dec. 6, 1995, now abandoned, which is a continuation of U.S. patent application Ser. No. 08/306,083, filed Sep. 14, 1994, now abandoned.

FIELD OF THE INVENTION

This invention relates to a process for the production of carriers for surface plasmon resonance (SPR).

BACKGROUND OF THE INVENTION

Surface plasmon resonance or (SPR) is a technique which can be used in the analysis of antibodies which are deposited on surfaces which have been coated with thin films of silver. SPR based sensors are discussed in a paper by I Faulkner, W. R. Flavell, J. Davies, R. F. Sunderland and C. S. Nunnerly: "SPR-based sensors studied by electron energy loss spectroscopy and attenuated total reflection"—published in J. Electron Spectroscopy, 1993. The manner in which a coating is applied to a surface has important consequences for the subsequent properties of that surface in terms of SPR and control of the coating process is important. At present, coating is generally performed by spattering but control is not good. It is important that the films are formed from uniform layers of metal in order to get reproducible SPR. On account of this improved methods for the production of films for SPR are desirable.

SUMMARY OF THE INVENTION

According to the present invention we provide a process for the production of a carrier for surface plasmon resonance analysis (SPR) comprising:

A) depositing a metallic film comprising silver on a surface, and

B) subjecting the film to an annealing step in which it is heated to a temperature sufficient to anneal it.

DETAILED DESCRIPTION OF THE INVENTION

Figure 1:
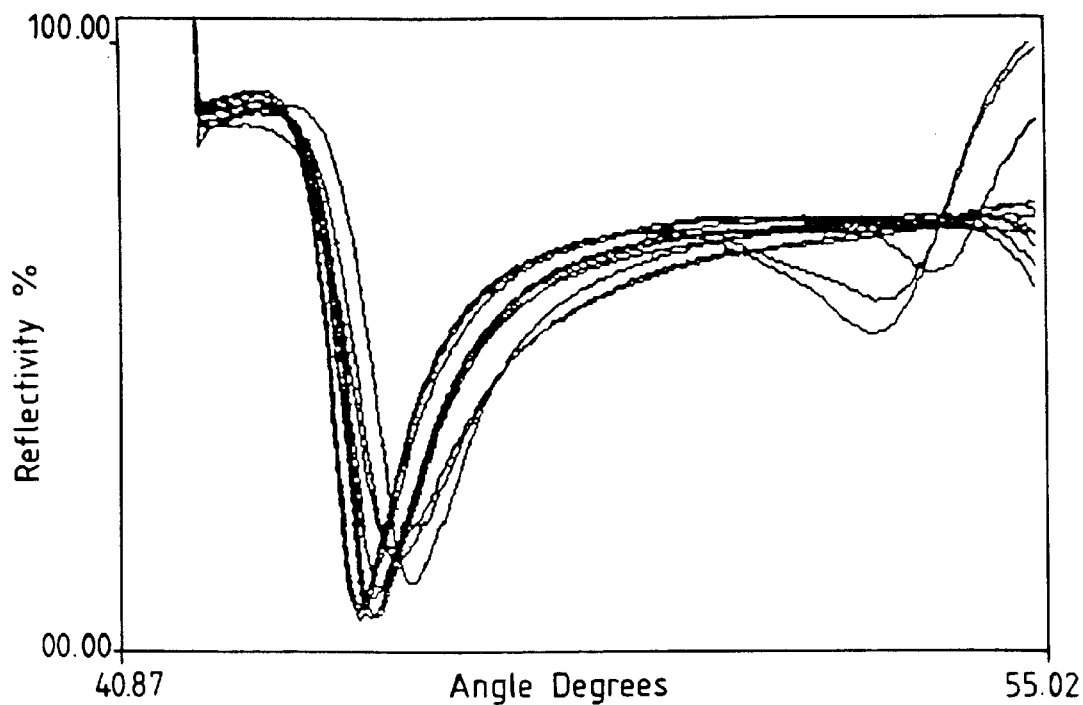
FIG. 1 relates to an air SPR of typically commercially available slides of approximately 410 Å gold (measured by optical density) with assay material removed from the gold surface.

In the annealing step the film is annealed effectively in order to bake it and thereby to orient the film and enhance its physical properties.

In operation of the process of the invention the surface, which is suitably a glass surface, is preferably subjected to an appropriate pre-treatment before the silver layer is laid down upon it. A suitable pre-treatment comprises the steps of cleaning, treatment by reactive glow discharge and thereafter deposition of a preparatory metallic layer. The preparatory metallic layer is preferably thin. The silver layer is then deposited on the preparatory layer. After the silver layer has been deposited it is annealed.

The annealing step is carried out effectively to bake the metallic film. It has the effect of orienting the film and enhancing its physical properties. Suitably annealing is effected by infra red heating in a chamber. The preferred period is in the range 1.5 to 4 hours. The preferred temperature is in the range 125° to 175° C. A temperature of 150° is especially preferred The annealing temperature is important when SPR is to be used to analyze the binding of antibodies. It is less important for analyzing the binding of compounds such as dextran.

Preferably the surface is a glass surface. Any suitable glass surface may be used but a preferred surface has a silicon dioxide surface layer. Particularly suitable types of glass are "PERMABLOC"™ and the earlier product "PERMASHEET"™ glass, both manufactured by Pilkington Glass of St. Helens, England. These have consistent top layers of silicon dioxide.

In the pre-treatment the glass can be cleaned by any suitable.means. Preferred treatments include treating with a freon and/or ultrasonic treatment and thereafter with a vapour bath or blow drying.

After cleaning the glass is suitably subjected to treatment with an oxygen-containing gas. Any suitable treatment may be used which will cause oxygen ions to enter the surface to an extent sufficient to sensitize it. Preferably the surface is subjected to a reactive glow discharge treatment which suitably uses a mixture of oxygen and an inert gas in particular argon. The surface can be put into a vacuum system in a clean room environment. It may then be subjected to reactive glow discharge using a mixture of oxygen and a rare gas containing suitably 5% to 15% oxygen. A preferred treatment uses a mixture of argon (90%) and Oxygen (10%). The treatment time is suitably 1 to 5 minutes with 2 minutes being preferred. Prior to this procedure the chamber is suitably pumped to a high vacuum. The organic vapour is suitably low or negligible.

In the pre-treatment, when reactive glow discharge treatment has been completed a thin preparatory metallic layer suitably deposited on the glass to form a base for the silver layer. This preparatory layer suitably comprises a major proportion of titanium, nickel and/or chromium, preferably being composed essentially of one of these metals, nickel being preferred. It is suitably deposited using an electron beam source. Suitably it has a thickness in the range 20 Å to 40 Å, preferably 20 Å to 30 Å and especially 25 Å to 30 Å.

When any pre-treatment has been completed, the silver layer is deposited on the preparatory metallic layer, suitably soon and preferably immediately after the latter has been formed. Suitably the silver layer has a thickness in the range 500 Å to 600 Å, preferably 520 Å. This has been found to give the optimum SPR response. The deposit of the silver layer is suitably made at a low rate, being preferably at a rate between 0.5 Å and 5.0 Å per second and especially 1.0 Å per second.

The annealing step is carried out after the silver layer has been deposited. Preferably it is carried out immediately after the deposit of the silver layer but the presence of one or more intermediate steps is not precluded.

The invention is illustrated by the following example:

EXAMPLE

A sheet of "PERMASHEET"™ glass obtained from Pilkingtons Glass, St. Helens, England was cleaned by ultrasonic treatment with a freon liquid, followed by freon vapour drying to eliminate streaking marks.

The cleaned sheet was then put into a vacuum system in a clean room environment and evacuated to approximately $10^{-7}$m bar in an oil-free environment. It was then subjected to reactive glow discharge using a gaseous mixture comprising 90% argon and 10% oxygen for a 2 minute period. This was done by admitting a small amount of the gaseous mixture to the system and pumping at a pressure of 20 to 60 microns while applying a voltage of 300V to an electrode for 2 minutes. As a result of this treatment oxygen ions have sufficient energy to enter the surface of the glass and sensitize it. The equipment used was a Temescale 2550 coating system using a Telemark 4 crucible e-gun evaporator with Sycon controller.

After reactive glow discharge treatment the system was repumped to approximately $10^{-7}$ m bar. Then a thin layer of nickel from a 99.9% pure ingot produced by Materials Research Corporation (MCR) was laid down upon the glass surface using an electron beam source. A typical beam current was 60 mA at 10 KeV energy. The layer was 25 Å to 30 Å in thickness. Deposition time was 25 to 30 seconds at 1 Å per second.

Immediately after the layer of nickel had been laid down a layer of silver from a 99.9% pure ingot from MCR was laid upon it using the same technique. A typical beam current was 50 mÅ at 10 KeV. The silver layer was 520 Å in thickness. Deposition time was 8.5 minutes at 1 Å per second.

After deposit of the silver layer annealing was effected by placing the coated glass surface in a chamber and subjecting it to infra red heating at 150° C. for 4 hours.

The silver coated glass surface produced had a very suitable SPR response.

Figure 2:
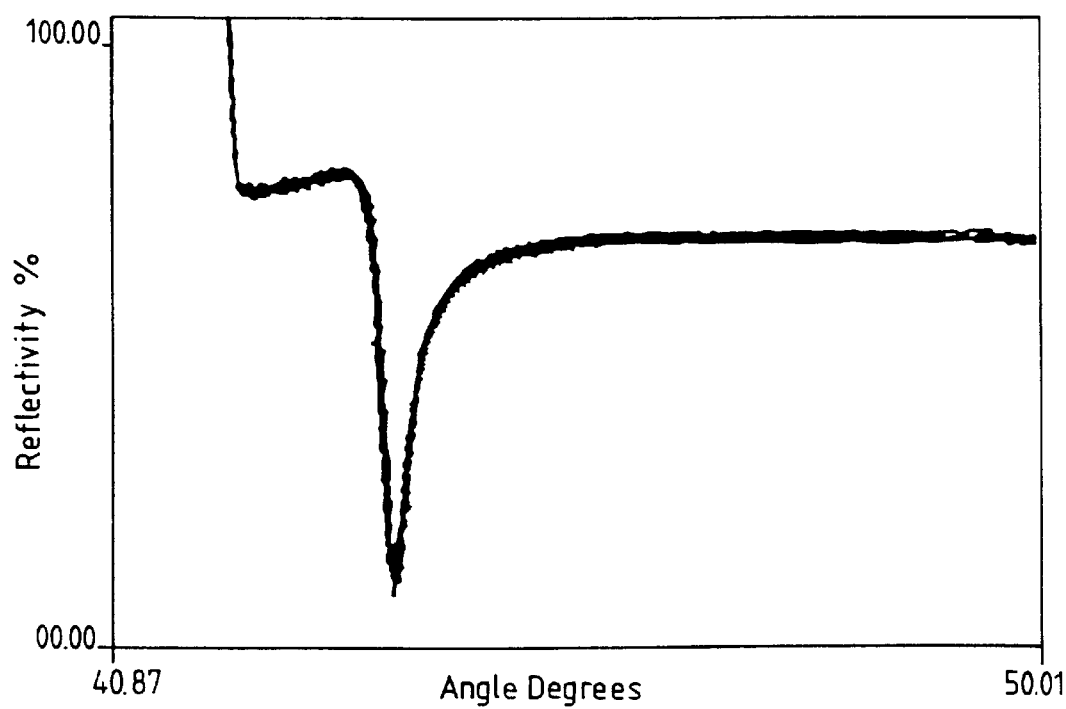
FIG. 2 relates to air SPR and to slides prepared by the process of the invention of approximately 560 Å silver with underlay measured by optical density.

This is illustrated by FIGS. 1 and 2 of the accompanying drawings wherein:

FIG. 1 is a graph of percentage light transmitted against angular position for a conventional commercially available SPR system; and FIG. 2 is a graph of percentage light transmitted against angular position for the system of the Example.

The Figures show that the characteristics produced by the Example are superior, giving a sharper, more distinct minimum in the curve.

This invention has been described in detail with particular reference to the preferred embodiments thereof, but it will be understood that variations and modifications can be effected within the spirit and scope of the invention.

I claim:

1. A process for the production of a carrier for surface plasmon resonance analysis comprising:

A. depositing a metallic film comprising silver on a surface, and
   B. subjecting said metallic film to an annealing step which results in said metallic film having a thickness of 500 Å to 600 Å.

2. The process of claim 1 wherein during the annealing step, said film is heated for a period of from 1.5 to 4 hours.

3. The process of claim 1 wherein during the annealing step, said film is heated to a temperature of from 125° to 175° C.

4. The process of claim 1 wherein said surface is coated with a silicon dioxide surface layer.

5. The process of claim 1 wherein a preparatory metallic layer comprising a major proportion of titanium, nickel or chromium is deposited on said surface before said silver layer is deposited.

6. The process of claim 5 wherein said preparatory metallic layer is formed essentially from nickel.

7. The process of claim 5 wherein said preparatory metallic layer has a thickness of from 20 Å to 40 Å.

8. The process of claim 1 wherein before said silver layer is deposited, said surface is subjected to a pre-treatment comprising the steps of cleaning, treatment by reactive glow discharge, and deposition of a preparatory metallic layer.

9. The process of claim 8 wherein said reactive glow discharge treatment uses a mixture of oxygen and argon containing 5% to 15% oxygen.

\* \* \* \* \*